(12) United States Patent
Griffith et al.

(10) Patent No.: US 11,890,138 B2
(45) Date of Patent: Feb. 6, 2024

(54) HANDHELD ULTRASOUND DEVICE AND REPLACEABLE TIPS THEREFOR

(71) Applicant: Remington Medical, Inc., Alpharetta, GA (US)

(72) Inventors: Nathan Christopher Griffith, Johns Creek, GA (US); Santiago Gallo, Roswell, GA (US); Basil Blythe Bonner, II, Cumming, GA (US); Parker Lee Aycock, Atlanta, GA (US)

(*) Notice: Subject to any disclaimer, the term of this patent is extended or adjusted under 35 U.S.C. 154(b) by 516 days.

(21) Appl. No.: 16/220,009

(22) Filed: Dec. 14, 2018

(65) Prior Publication Data

US 2019/0374200 A1    Dec. 12, 2019

Related U.S. Application Data

(60) Provisional application No. 62/681,781, filed on Jun. 7, 2018.

(51) Int. Cl.
*A61B 8/00* (2006.01)
*A61B 8/08* (2006.01)
*A61B 8/06* (2006.01)

(52) U.S. Cl.
CPC .......... *A61B 8/4427* (2013.01); *A61B 8/4422* (2013.01); *A61B 8/4472* (2013.01);
(Continued)

(58) Field of Classification Search
CPC ....... A61B 8/06; A61B 8/4411; A61B 8/4422; A61B 8/4427; A61B 8/4472;
(Continued)

(56) References Cited

U.S. PATENT DOCUMENTS 5,423,747 A * 6/1995 Amano ............... A61M 60/585
604/246
5,490,522 A 2/1996 Dardel
(Continued)

FOREIGN PATENT DOCUMENTS

EP      0940116 A1    9/1999
WO   WO 92/07515    5/1992
(Continued)

OTHER PUBLICATIONS

International Search Report and Written Opinion PCT/US2019/031015, dated Jun. 19, 2019. (24 pages).
(Continued)

*Primary Examiner* — Yi-Shan Yang
*Assistant Examiner* — Alexei Bykhovski
(74) *Attorney, Agent, or Firm* — Dority & Manning, P.A.

(57) ABSTRACT

Handheld ultrasound devices and replaceable tips for such devices are provided. For example, a handheld ultrasound device comprises a handle and a tip that includes a sensor for transmitting and receiving ultrasound waves. The handle and the tip may be a single, integral, unit or the tip may be separable from the handle. In either embodiment, the handle and tip together are a fully self-contained unit. Also provided are handheld ultrasound sterile assemblies, comprising a handheld ultrasound device and a sheath that fully covers the device to provide a sterile barrier for the device. Further, tips for handheld ultrasound devices are provided. The tips may be a replaceable component of the handheld ultrasound devices. For example, the tips may be configured for one-time use, and the tip rather than the entire handheld ultrasound device may be replaced between procedures such that a new tip is used in a subsequent procedure.

18 Claims, 18 Drawing Sheets

(52) U.S. Cl.
CPC .............. *A61B 8/4483* (2013.01); *A61B 8/06* (2013.01); *A61B 8/462* (2013.01); *A61B 8/463* (2013.01); *A61B 8/488* (2013.01); *A61B 8/56* (2013.01)

(58) Field of Classification Search
CPC ....... A61B 8/4483; A61B 8/462; A61B 8/463; A61B 8/488; A61B 8/56
See application file for complete search history.

(56) References Cited

U.S. PATENT DOCUMENTS

| | | | |
|---|---|---|---|
| 5,570,692 A | | 11/1996 | Morinaga |
| 5,634,466 A | * | 6/1997 | Gruner ................. A61B 8/4411 600/467 |
| 6,309,358 B1 | | 10/2001 | Okubo |
| 2003/0018262 A1 | * | 1/2003 | Manor .................... A61B 8/06 600/449 |
| 2003/0097071 A1 | | 5/2003 | Halmann et al. |
| 2005/0261582 A1 | | 11/2005 | Becker et al. |
| 2010/0204569 A1 | | 8/2010 | Burnside et al. |
| 2011/0313282 A1 | | 12/2011 | Frankel et al. |
| 2012/0059394 A1 | | 3/2012 | Brenner et al. |
| 2012/0179044 A1 | * | 7/2012 | Chiang .................. A61B 8/145 600/447 |
| 2012/0271294 A1 | * | 10/2012 | Barthe .................. A61B 8/461 606/28 |
| 2013/0158363 A1 | | 6/2013 | Zoghbi |
| 2014/0213936 A1 | * | 7/2014 | Monovoukas ......... A61B 5/445 600/587 |
| 2015/0025451 A1 | * | 1/2015 | Banko .................... A61M 1/774 604/35 |
| 2016/0270904 A1 | * | 9/2016 | Neusidl ................. A61F 2/148 |
| 2017/0093190 A1 | | 3/2017 | Miller et al. |
| 2017/0296142 A1 | | 10/2017 | Wodecki et al. |
| 2018/0214130 A1 | * | 8/2018 | Hossack ............. A61B 8/0891 |
| 2018/0228553 A1 | * | 8/2018 | Bai ........................ A61B 34/30 |
| 2018/0279996 A1 | * | 10/2018 | Cox ........................ A61B 8/483 |
| 2020/0008775 A1 | * | 1/2020 | Erkamp ............... A61B 8/4254 |
| 2020/0261059 A1 | * | 8/2020 | Xu ............................ A61B 8/06 |

FOREIGN PATENT DOCUMENTS

| | | |
|---|---|---|
| WO | WO 96/14014 | 5/1996 |
| WO | WO 99/35968 A1 | 7/1999 |
| WO | WO 03/007820 | 1/2003 |
| WO | WO 2010/096174 A1 | 8/2010 |

OTHER PUBLICATIONS

International Preliminary Report on Patentability and Written Opinion; PCT/US2019/031016, dated Dec. 8, 2020, 6 pages.
International Preliminary Report on Patentability and Written Opinion; PCT/US2019/031015, dated Dec. 8, 2020, 6 pages.
U.S. Appl. No. 16/220,002, filed Dec. 14, 2018.
U.S. Appl. No. 16/220,025, filed Dec. 14, 2018.

* cited by examiner

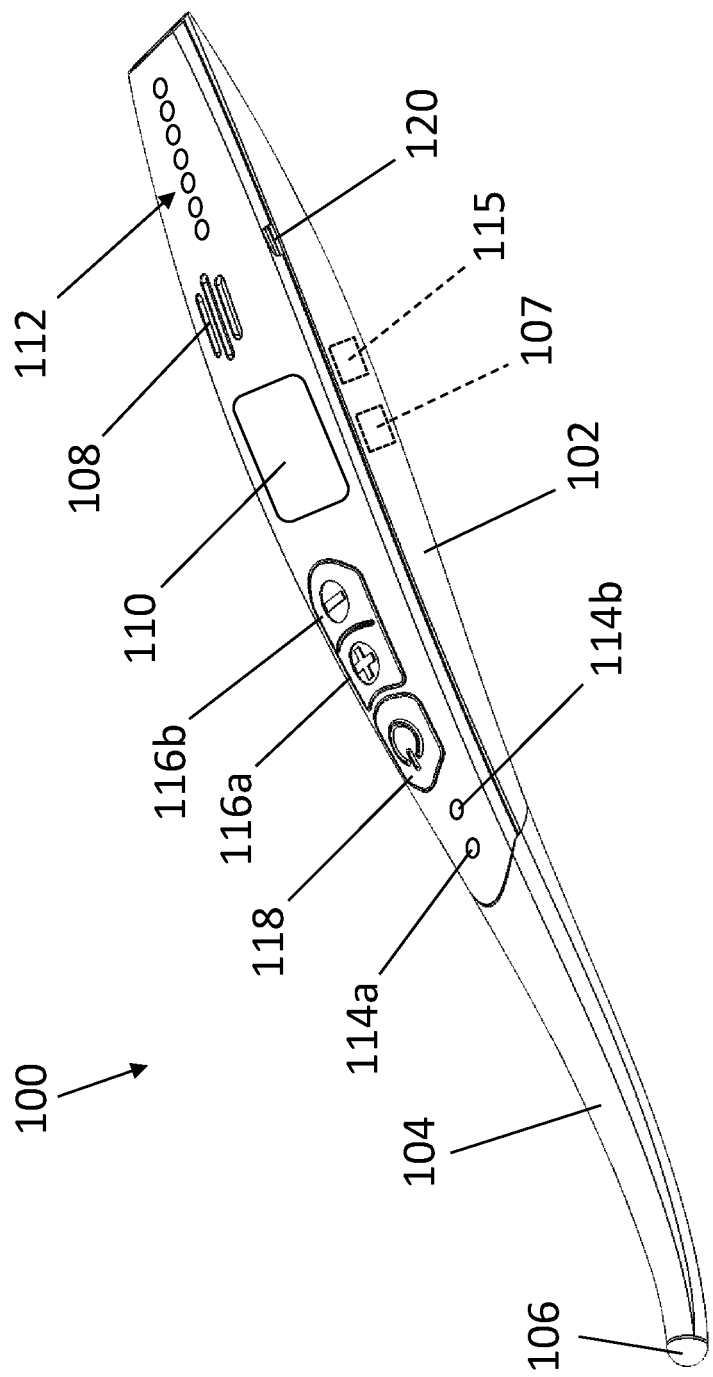
– FIG. 1 –

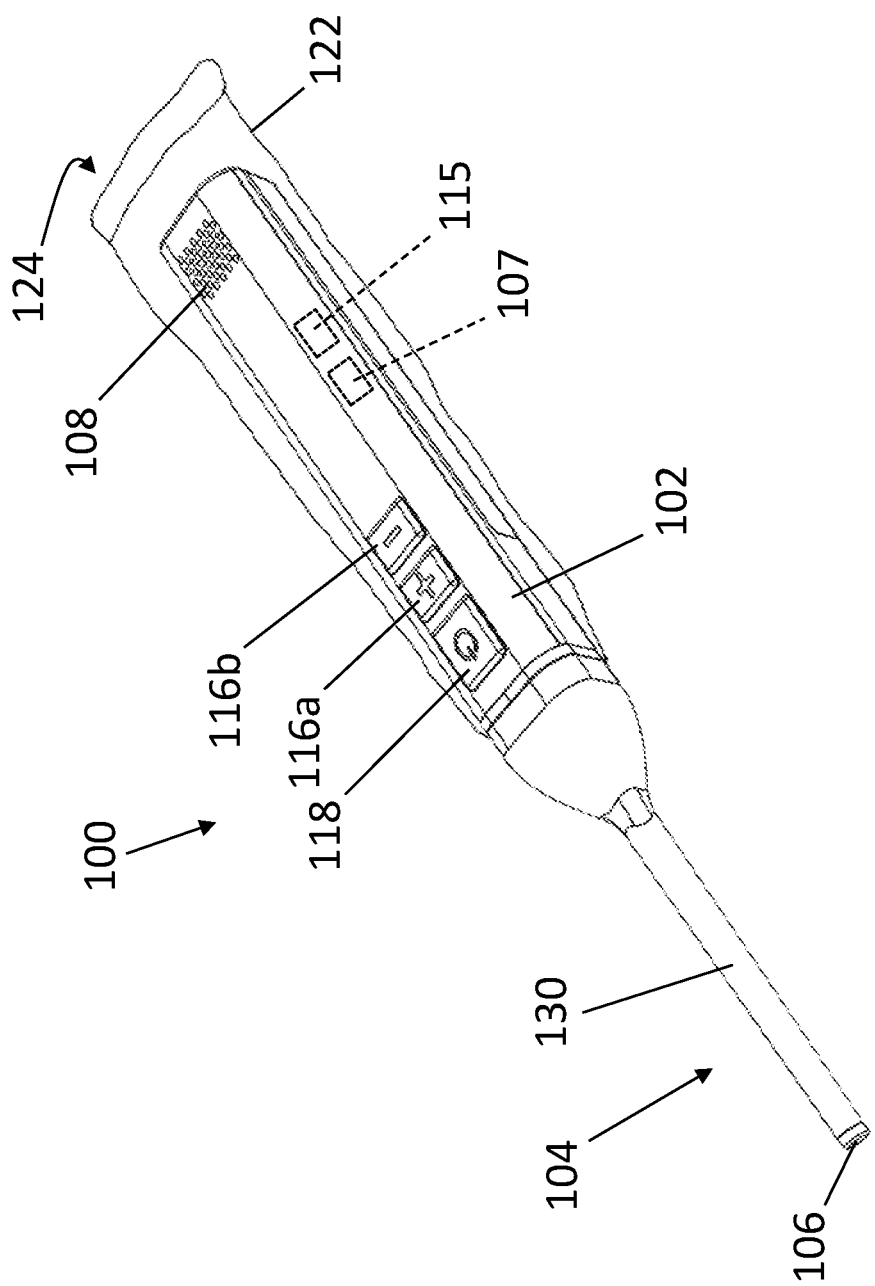
— FIG. 2 —

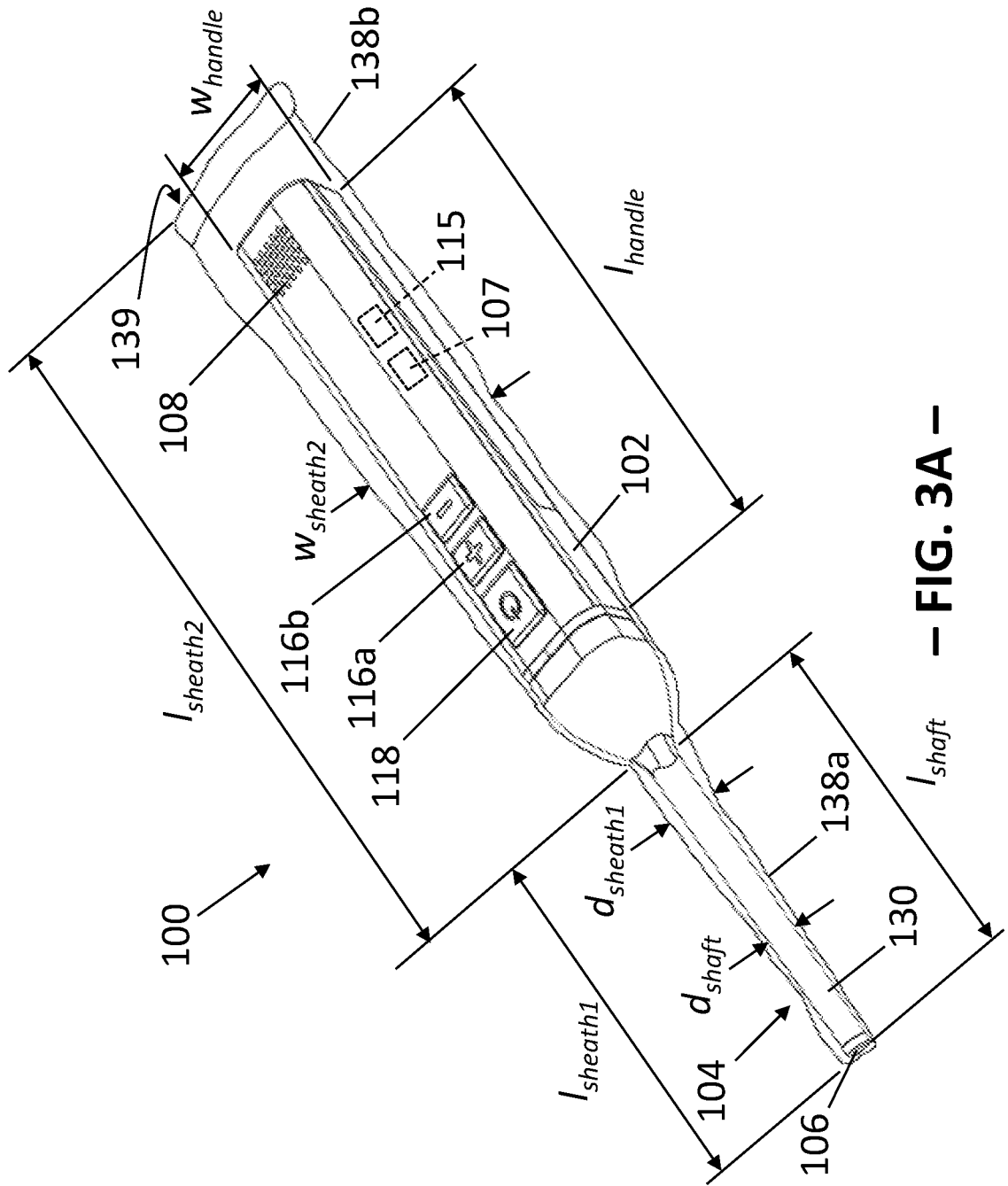
— FIG. 3A —

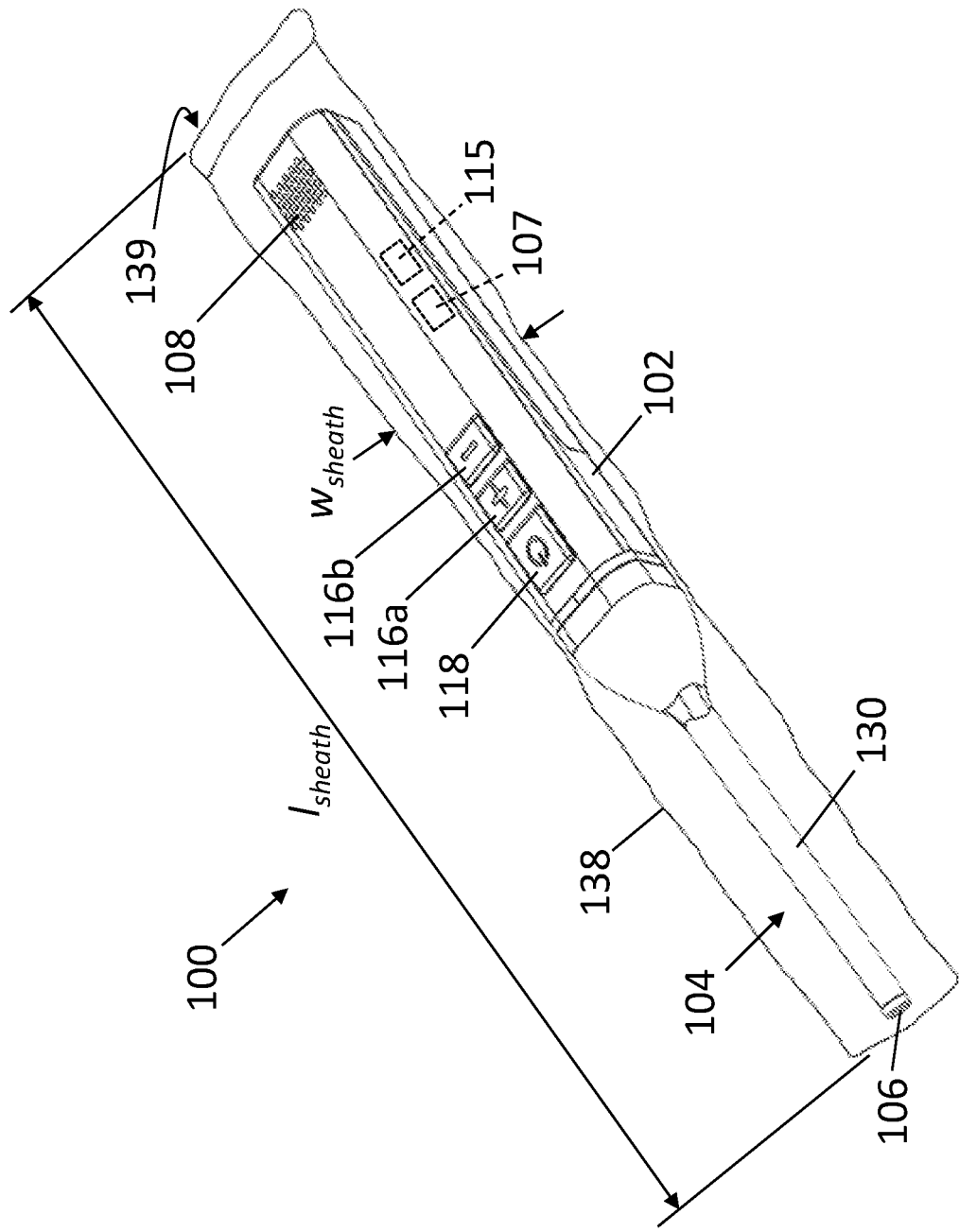
– FIG. 3B –

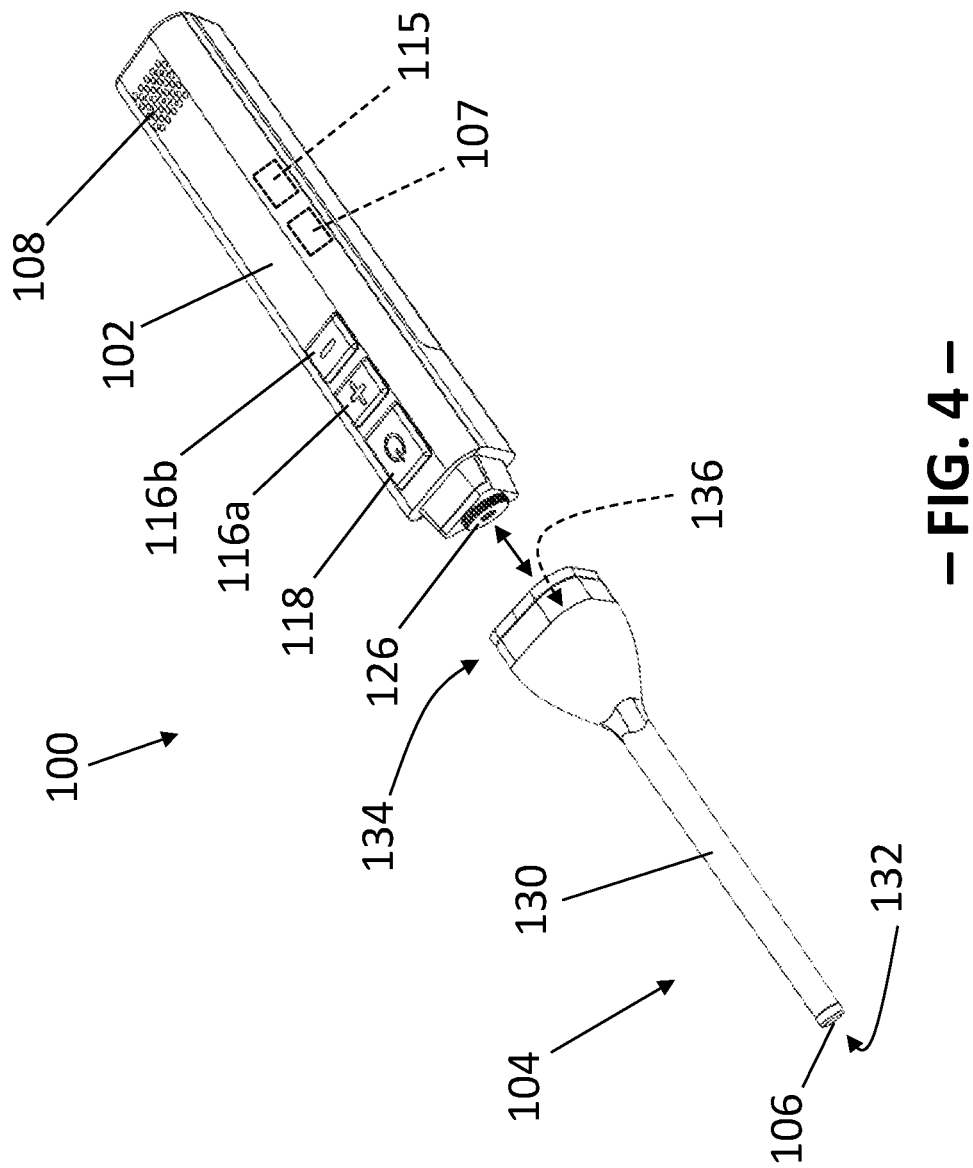
– FIG. 4 –

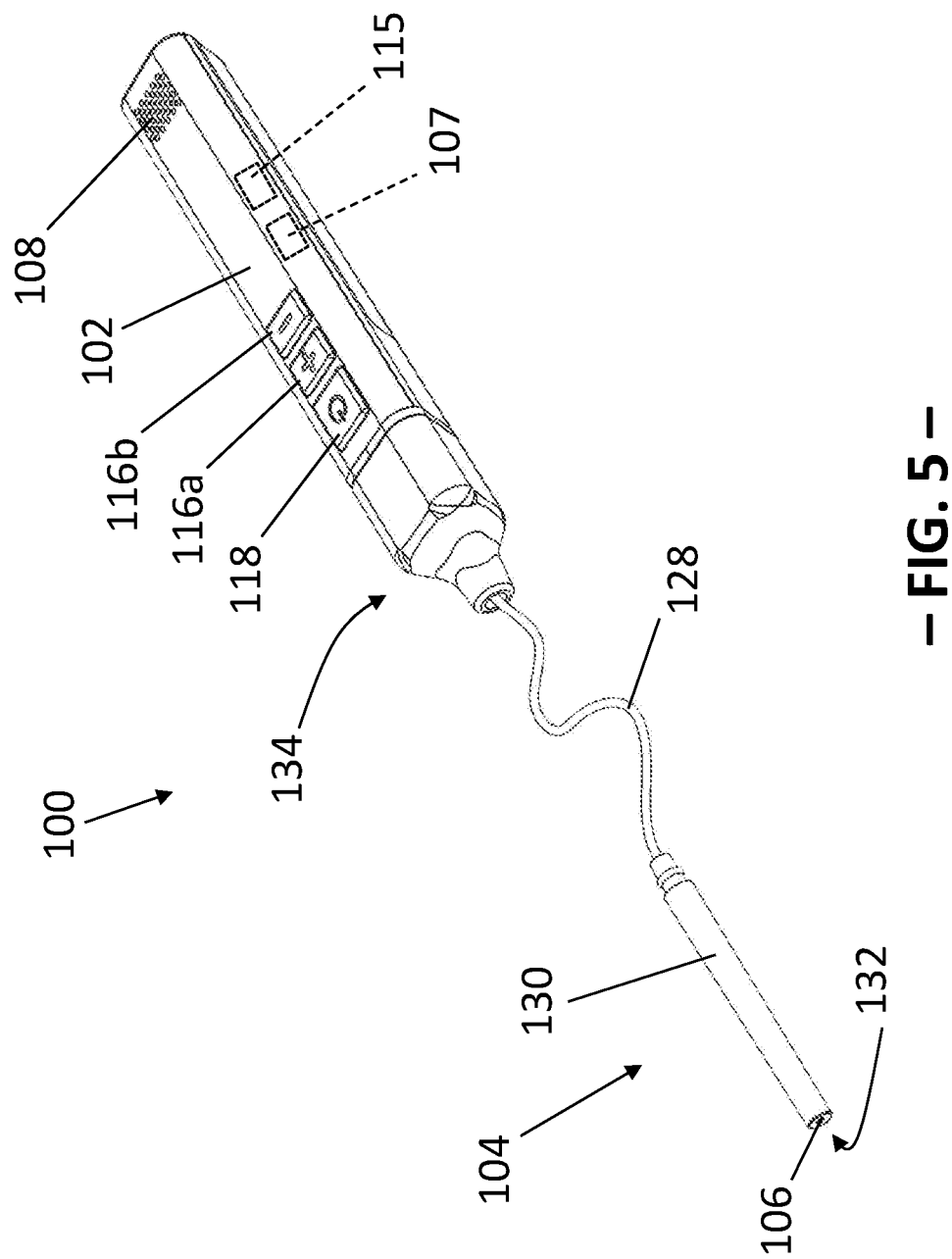
– FIG. 5 –

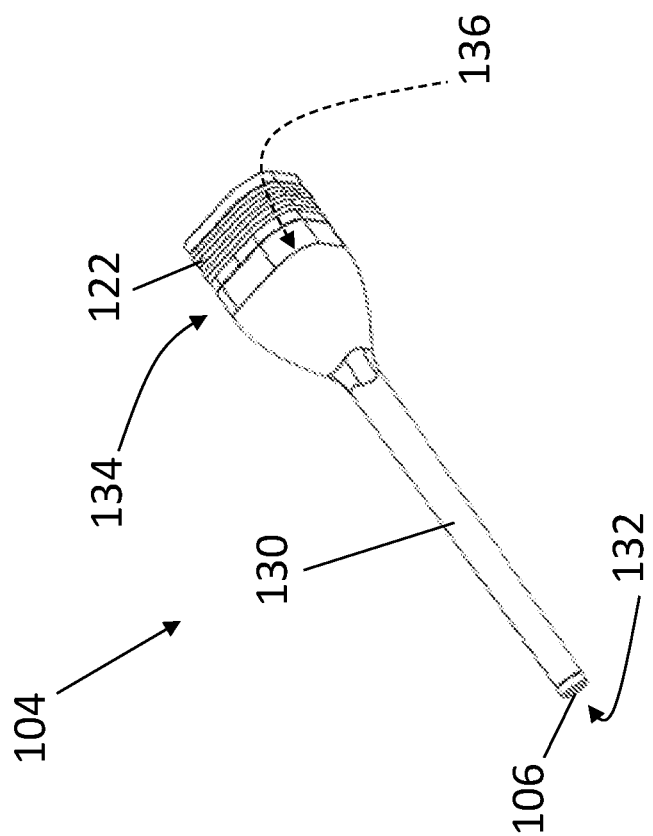
– FIG. 6 –

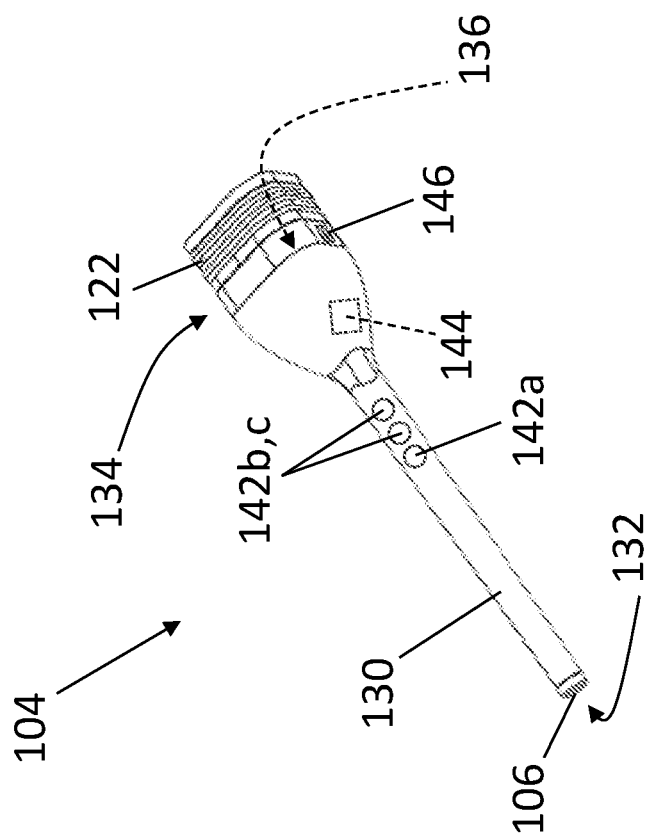
– FIG. 7 –

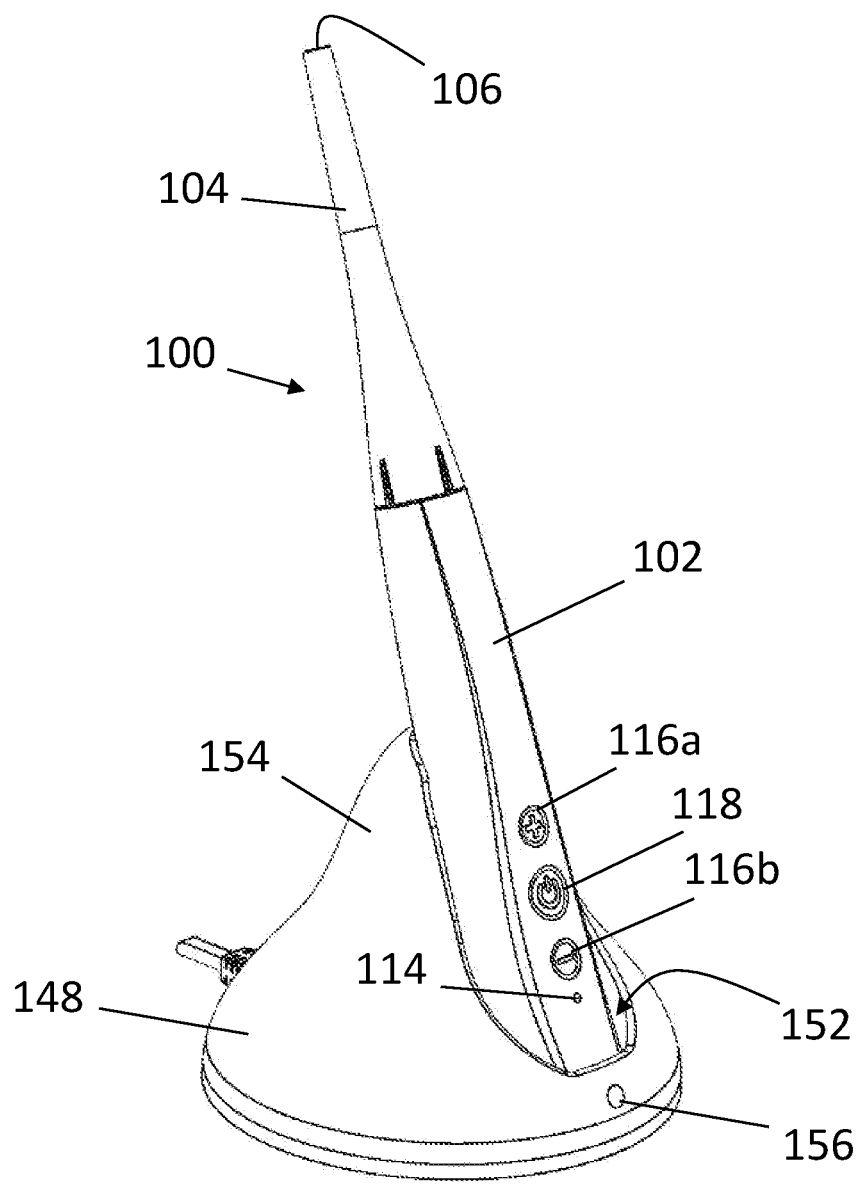
- FIG. 8 -

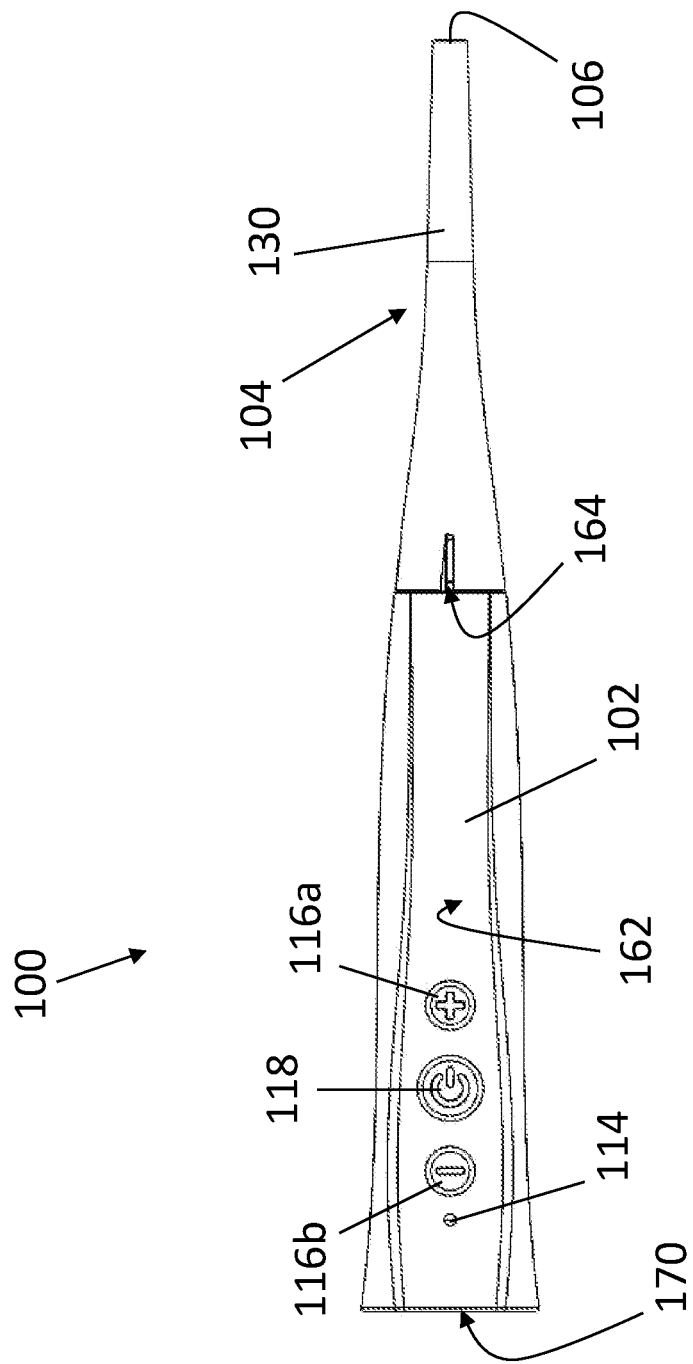
- FIG. 9 -

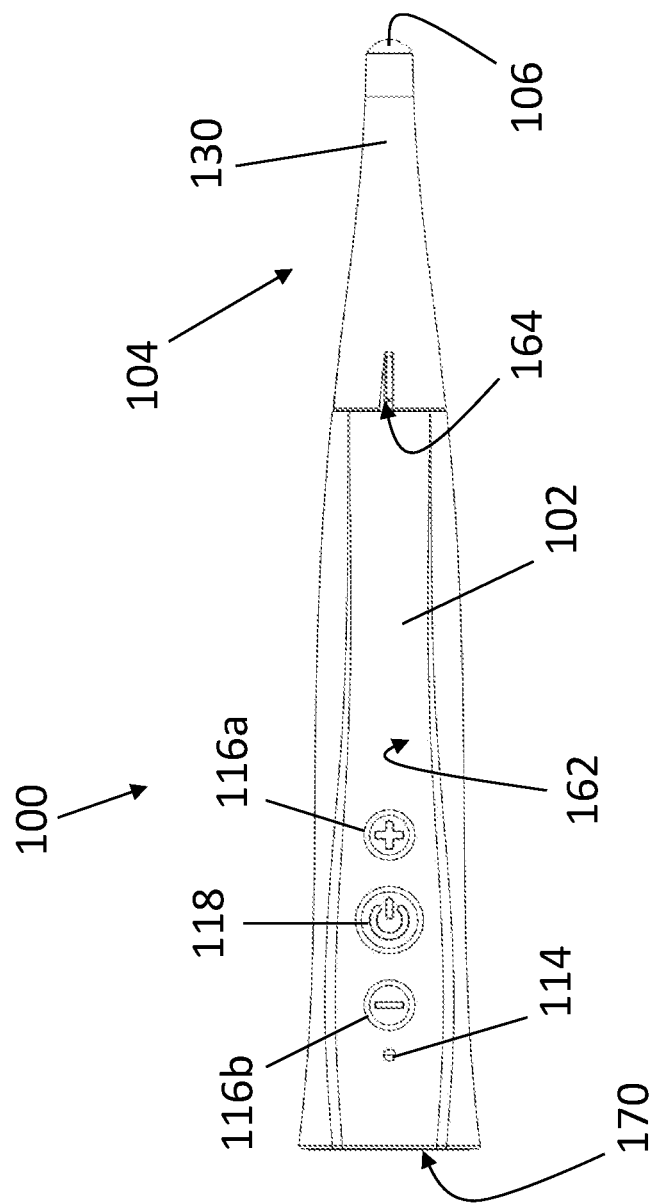
- FIG. 17 -

HANDHELD ULTRASOUND DEVICE AND REPLACEABLE TIPS THEREFOR

CROSS-REFERENCE TO RELATED APPLICATIONS

The present application claims priority to U.S. Provisional Application Ser. No. 62/681,781, filed on Jun. 7, 2018, which is incorporated herein in its entirety by reference thereto.

FIELD

The present subject matter relates generally to ultrasound devices. More particularly, the present subject matter relates to handheld ultrasound devices and replaceable tips for handheld ultrasound devices.

BACKGROUND

Doppler ultrasound may be used in surgical and clinical settings to assess the strength and pattern of blood flowing through vessels. Typically, a transducer probe or sensor translates electrical signals into waves of ultrasound at a specific frequency. When the ultrasound waves encounter flowing blood, they are reflected at a shifted frequency that varies with the velocity of the blood. The transducer probe translates this shifted frequency back into an electrical signal, which is processed by the device into an audible and/or visible signal corresponding to the velocity of the blood.

Usually, such Doppler ultrasound devices utilize a handheld or stationary enclosure that houses most of the electronics, speaker, and (if applicable) display. A separate probe is connected to the enclosure via a cable. Existing hand-held Doppler ultrasound devices cannot be used entirely within the sterile field of, e.g., an operating room (OR) because such devices are not designed to be entirely covered with a sterile barrier. Thus, a cord must connect a sterile sensor to the unsterile device that is located outside of the sterile field. Rather than the surgeon, a second operator is required to operate the device, and often, the second operator must operate competing devices. Further, the cord connecting the sterile sensor to the unsterile device can be a tripping hazard in the busy OR environment.

Accordingly, improved handheld ultrasound devices that may be used in sterile environments would be desirable. In particular, a handheld ultrasound device having a handle and a tip where the entire device is sterile would be beneficial. Further, a handheld ultrasound device having a handle and a removable tip where at least the tip is sterile would be useful. Replaceable sterile tips for a handheld ultrasound device that may incorporate a sterile barrier for the reusable component of the device also would be advantageous.

BRIEF DESCRIPTION

Aspects and advantages of the invention will be set forth in part in the following description, or may be obvious from the description, or may be learned through practice of the invention.

In one aspect of the present subject matter, a handheld ultrasound device is provided. The handheld ultrasound device comprises a handle and a tip. The tip comprises a sensor for transmitting and receiving ultrasound waves. The handle and the tip are a single, integral, fully self-contained unit.

In some embodiments, the handheld ultrasound device further comprises a power source that is disposed within the handle. Moreover, the handle may include a speaker for emitting audible feedback of the received ultrasound waves. Alternatively or additionally, the handle includes a display for displaying visual feedback of the received ultrasound waves and/or a light array for providing visual feedback of the received ultrasound waves.

In further embodiments, the handheld ultrasound device is a sterile device configured for single patient use. In other embodiments, the handheld ultrasound device is a sterile device configured for re-sterilization after use.

Further, the handle may include one or more controls for operating the handheld ultrasound device. The one or more controls may include volume buttons for adjusting the volume of an audible feedback source and a power button for powering the handheld ultrasound device on and off. In still further embodiments, the handle comprises a port for connecting the handheld ultrasound device to a source for charging a rechargeable power source disposed in the handle.

In another aspect of the present subject matter, a handheld ultrasound device is provided. The handheld ultrasound device comprises a handle and a tip coupled to the handle. The tip comprises a sensor for transmitting and receiving ultrasound waves, and the tip is separable from the handle. The handle and tip are a fully self-contained unit.

In some embodiments, the tip is operatively coupled to the handle via a connector. In other embodiments, the tip is operatively coupled to the handle via a wireless connection. For example, the sensor may wirelessly transmit the ultrasound waves to a receiver disposed within the handle. In still other embodiments, the tip is tethered to the handle via a cable such that the tip is operable when separated from the handle. A distal end of the tip may define a cavity for storing the cable when the tip is attached to the handle.

In further embodiments, the tip is sterile and incorporates a sterile barrier for enclosing the handle. In some embodiments, the sterile tip is configured for re-sterilization after use. Alternatively, the sterile tip is configured for one-time use.

Moreover, the tip may be replaceable. In some embodiments, a plurality of different tips are configured for coupling to the handle, each tip of the plurality of different tips having a configuration for a particular medical procedure. In still further embodiments, the tip includes a shaft, and the sensor is positioned on a proximal end of the tip at one end of the shaft.

Further, a power source may be disposed within the handle. In other embodiments, a power source is disposed within the tip. Moreover, the handle may include a speaker for emitting audible feedback of the received ultrasound waves. Additionally or alternatively, the handle may include a display for displaying visual feedback of the received ultrasound waves and/or a light array for providing visual feedback of the received ultrasound waves.

In still other embodiments, the handle comprises one or more controls for operating the handheld ultrasound device. Additionally or alternatively, the tip comprises one or more controls for operating the handheld ultrasound device. The one or more controls may include volume buttons for adjusting the volume of an audible feedback source and a power button for powering the handheld ultrasound device on and off. Further, the handle may comprise a port for connecting the handheld ultrasound device to a source for charging a rechargeable power source disposed in the handle. Instead of or in addition to the port in the handle, the tip may comprise a port for connecting the handheld ultrasound device to a source for charging a rechargeable power source disposed in the tip.

In some embodiments, the tip includes a shaft, and the shaft is permanently deformable. Alternatively, the shaft is temporarily deformable. In other embodiments, the tip incorporates a curvature along a length of the tip. In further embodiments, the tip may be flexible, semi-flexible, rigid, or semi-rigid.

In another aspect of the present subject matter, a handheld ultrasound sterile assembly is provided. The handheld ultrasound sterile assembly comprises a handheld ultrasound device that includes a handle and a tip. The tip comprises a sensor for transmitting and receiving ultrasound waves. The handheld ultrasound sterile assembly further comprises a sheath. The sheath fully covers the handheld ultrasound device to provide a sterile barrier for the device.

In some embodiments, the handle and the tip are a single, integral, fully self-contained unit. In other embodiments, the tip is separable from the handle, but together, the handle and tip are a fully self-contained unit.

Further, the sheath may be shaped complementary to the handheld ultrasound device. For example, the sheath may comprise a first portion having a diameter and a length complementary to a diameter and a length of the tip of the handheld ultrasound device and a second portion having a width complementary to a width of the handle of the handheld ultrasound device.

In yet another aspect of the present subject matter, a tip for a handheld ultrasound device is provided. The tip comprises a sensor for transmitting and receiving ultrasound waves, a shaft, and a connector for operatively connecting the tip to a handle of the handheld ultrasound device. The sensor is positioned on a proximal end of the tip at one end of the shaft.

For instance, the tip may be a replaceable component of the handheld ultrasound device. Further, the tip may be sterile and incorporate a sterile barrier for enclosing the handle. In some embodiments, the sterile barrier is folded before the tip is attached to the handle.

In further embodiments, the tip is tethered to the handle via a cable such that the tip is operable when separated from the handle. A distal end of the tip may define a cavity for storing the cable when the tip is attached to the handle. In some embodiments, the tip comprises the cable, but in other embodiments, the handle comprises the cable.

In still further embodiments, the tip is sterile and is configured for re-sterilization after use. Alternatively, the tip is sterile and is configured for one-time use. The tip may be configured for use in a particular medical procedure.

Moreover, the shaft may be permanently or temporarily deformable. Further, in some embodiments, the tip incorporates a curvature along a length of the tip. The tip may be flexible, semi-flexible, rigid, or semi-rigid.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a side, perspective view of a single piece handheld ultrasound device, according to an exemplary embodiment of the present subject matter.

FIG. 2 provides a side, perspective view of a handheld ultrasound device comprising a separable tip and a sterile barrier drawn over a handle of the device, according to an exemplary embodiment of the present subject matter.

FIG. 3A provides a side, perspective view of a handheld ultrasound sterile assembly comprising a sheath and the device of FIG. 2 without the sterile barrier, wherein the sheath provides a sterile barrier between the device and a patient, according to an exemplary embodiment of the present subject matter in which the sheath has a shape complementary to the shape of the device.

FIG. 3B provides a side, perspective view of the assembly of FIG. 3A according to an exemplary embodiment of the present subject matter in which the sheath has a same width over its length.

FIG. 4 provides a side, perspective view of the device of FIG. 2, with the tip separated from the handle and the sterile barrier omitted for clarity.

FIG. 5 provides a side, perspective view of a handheld ultrasound device comprising a separable tethered tip, according to an exemplary embodiment of the present subject matter.

FIG. 6 provides a side, perspective view of a replacement tip for a handheld ultrasound device, the replacement tip having a sterile barrier, according to an exemplary embodiment of the present subject matter.

FIG. 7 provides a side, perspective view of the replacement tip of FIG. 6 comprising a power source and a plurality of controls for controlling the handheld ultrasound device, according to an exemplary embodiment of the present subject matter.

FIG. 8 provides a perspective view of a handheld ultrasound device, according to an exemplary embodiment of the present subject matter, received in an exemplary docking station.

FIG. 9 provides a front view of the handheld ultrasound device of FIG. 8.

FIG. 17 provides a front view of a handheld ultrasound device according to an exemplary embodiment of the present subject matter, the device having a shorter tip and more rounded tip sensor than the device of FIGS. 8-16.

DETAILED DESCRIPTION

Figure 10:
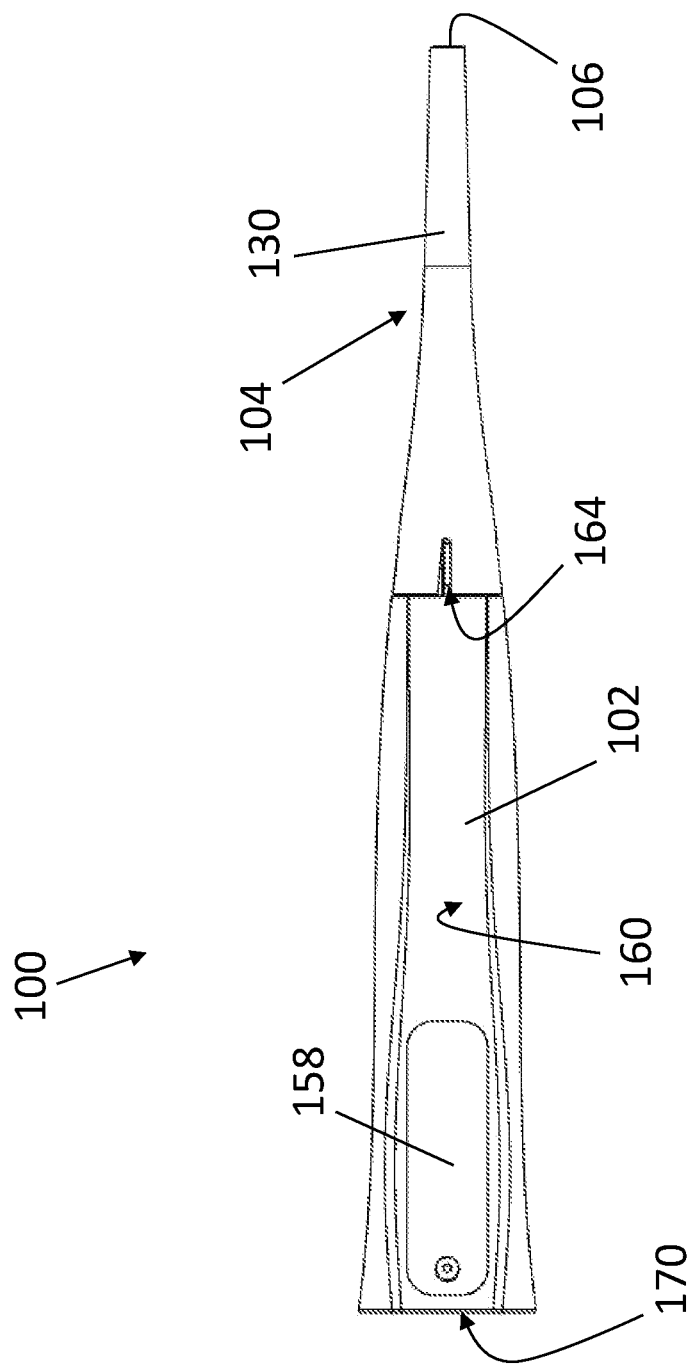
FIG. 10 provides a back view of the handheld ultrasound device of FIG. 8.
Figure 11:
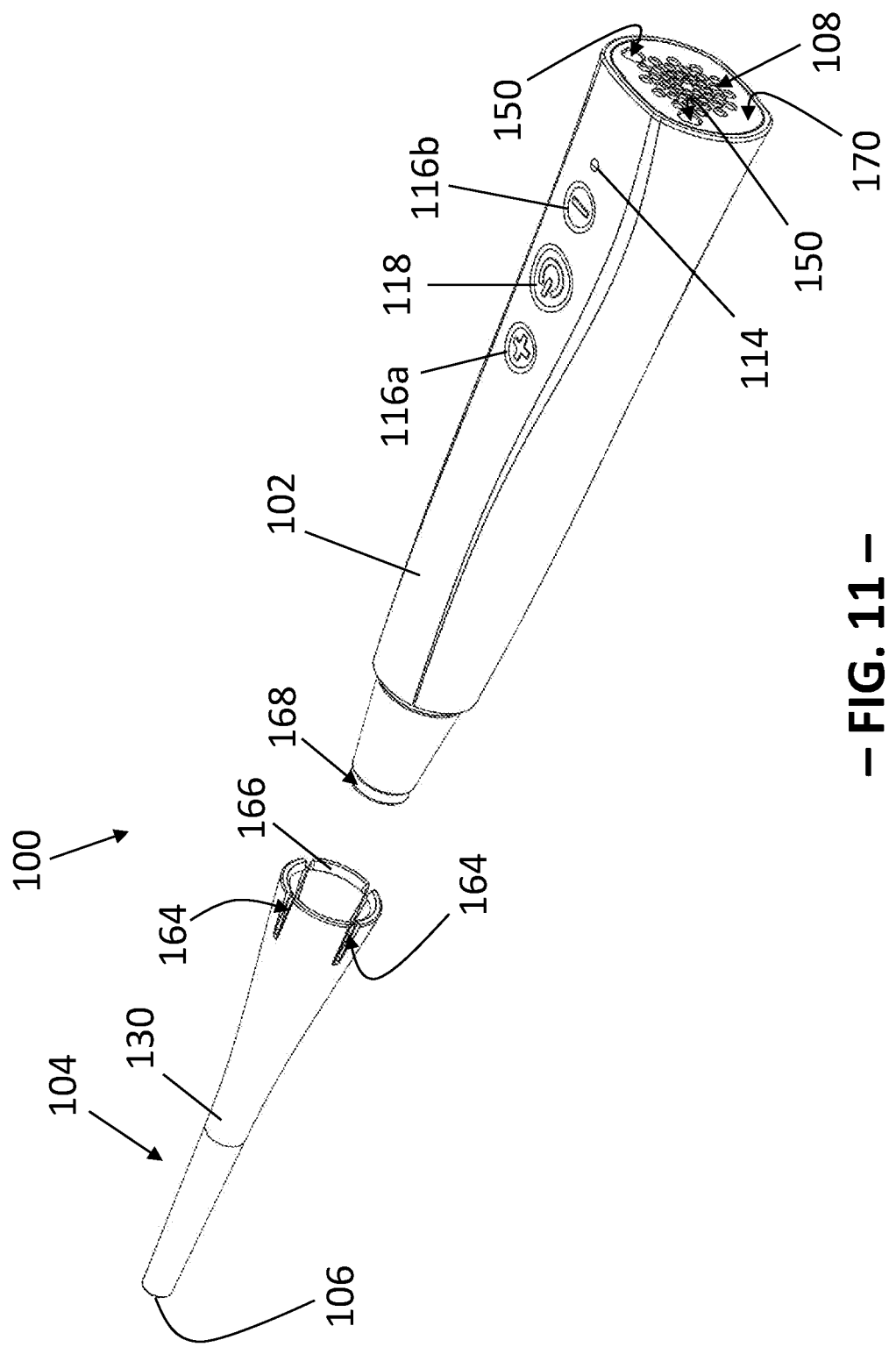
FIG. 11 provides a handle end, perspective view of the handheld ultrasound device of FIG. 8, with a tip of the device separated from a handle of the device.
Figure 12:
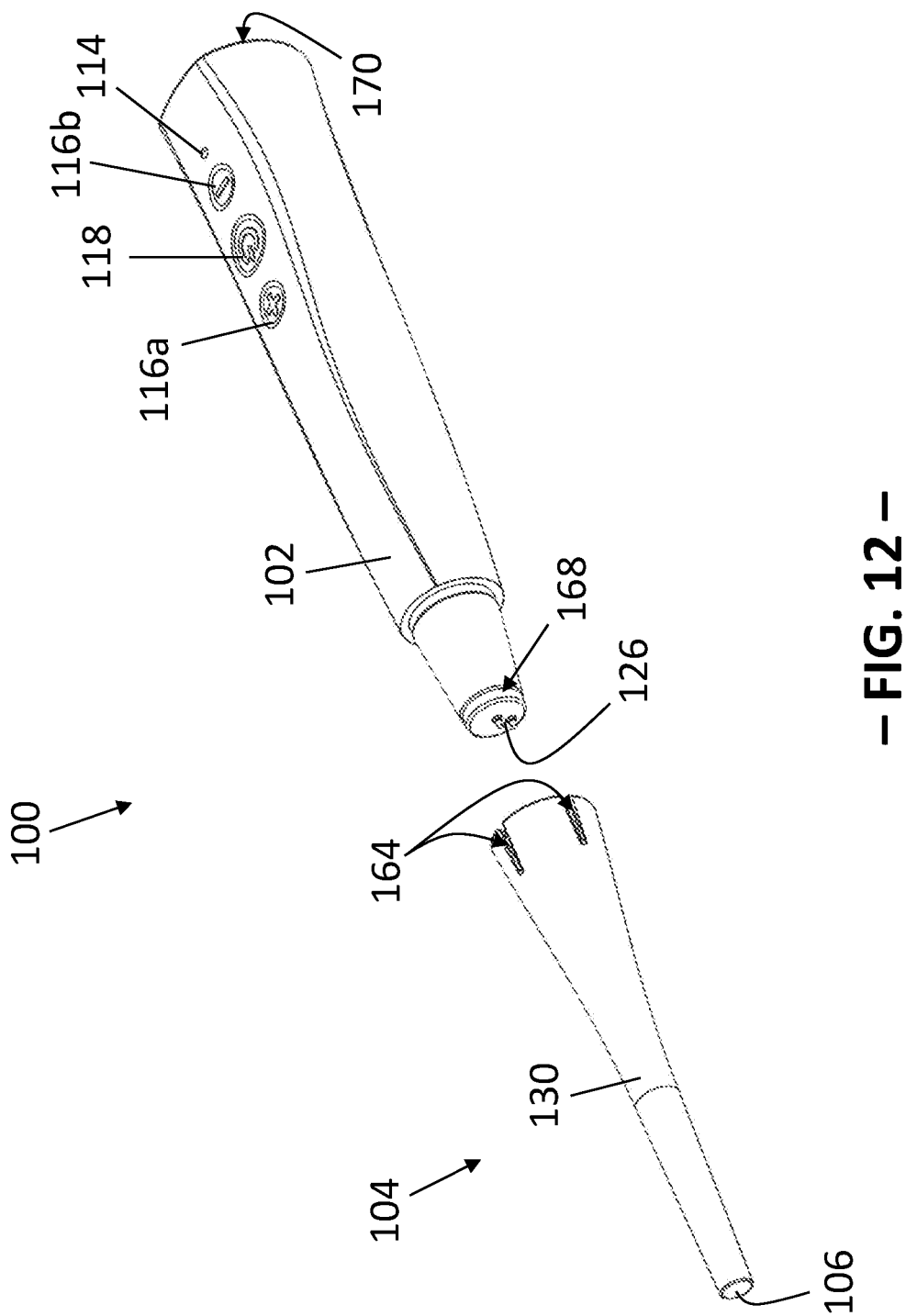
FIG. 12 provides a tip end, perspective view of the handheld ultrasound device of FIG. 8, with the tip separated from the handle.
Figure 13:
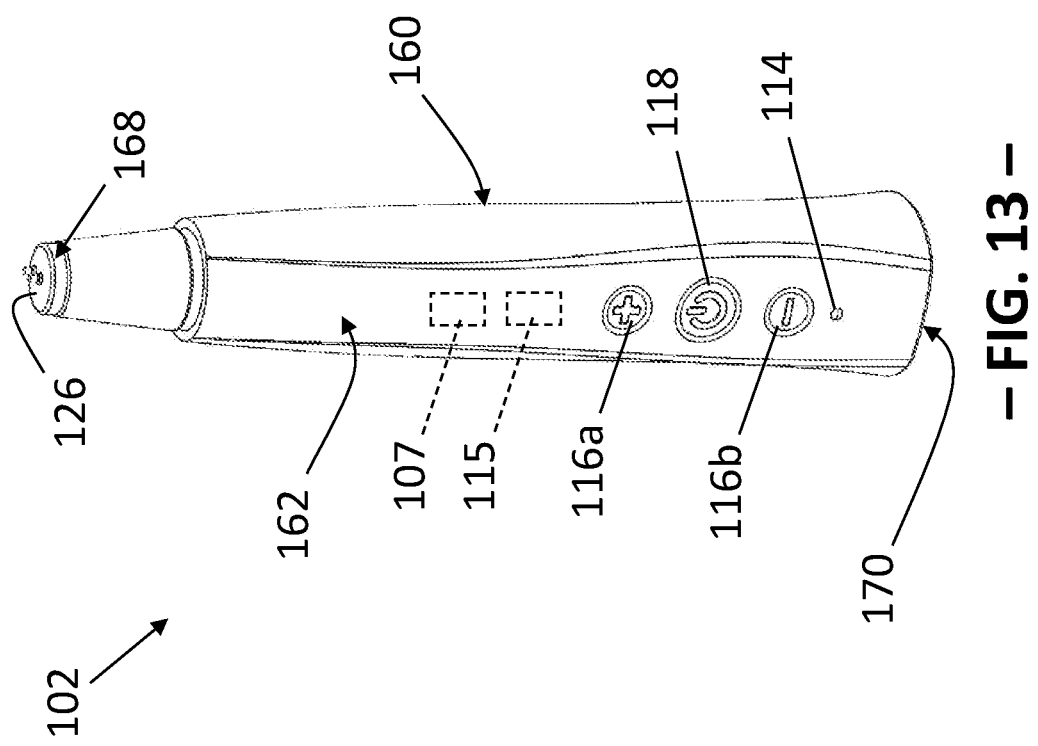
FIG. 13 provides a perspective view of the handle of the handheld ultrasound device of FIG. 8.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention.

As used herein, the terms "first," "second," and "third" may be used interchangeably to distinguish one component from another and are not intended to signify location or importance of the individual components.

The terms "upstream" and "downstream" refer to the relative direction with respect to fluid flow in a fluid pathway. For example, "upstream" refers to the direction from which the fluid flows, and "downstream" refers to the direction to which the fluid flows.

The terms "coupled," "fixed," "attached to," and the like refer to both direct coupling, fixing, or attaching, as well as indirect coupling, fixing, or attaching through one or more intermediate components or features, unless otherwise specified herein.

The singular forms "a," "an," and "the" include plural references unless the context clearly dictates otherwise.

Approximating language, as used herein throughout the specification and claims, is applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value, or the precision of the methods or machines for constructing or manufacturing the components and/or systems. For example, the approximating language may refer to being within a 10 percent margin.

Here and throughout the specification and claims, range limitations are combined and interchanged, such ranges are identified and include all the sub-ranges contained therein unless context or language indicates otherwise. For example, all ranges disclosed herein are inclusive of the endpoints, and the endpoints are independently combinable with each other.

Referring now to the drawings, wherein identical numerals indicate the same elements throughout the figures, FIG. 1 is a side perspective view of a handheld ultrasound device 100 according to an exemplary embodiment of the present subject matter. In the depicted embodiment, the device 100 has a stylus-like form factor and includes a handle 102 and an integral tip 104. As shown in FIG. 1 and described herein, the handle 102 provides a housing for the various electronics of the device 100, which may include a power source, one or more processors, one or more signal transmitters and/or receivers, etc., and thus, the handle 102 may be referred to as a transceiver. The tip 104 incorporates a sensor 106; in an exemplary embodiment, the sensor 106 is a piezoelectric transducer for sensing the strength and/or pattern of blood flow through a blood vessel. More particularly, the sensor 106 translates electrical signals into ultrasound waves at a specific frequency. When the ultrasound waves encounter flowing blood, they are reflected at a shifted frequency that varies with the velocity of the blood. The sensor 106 translates this shifted frequency back into an electrical signal that is processed by the device 100 into an audible, visible, or other signal or feedback corresponding to the velocity of the blood. For instance, a suitable processor may be housed in the handle 102 of the device 100 that converts the electrical signals from the sensor 106 into an audible signal delivered to an operator through, e.g., a speaker 108 and/or into a visual signal delivered to the operator through, e.g., a display 110 and/or a light array 112. More specifically, the handle 102 may include a control circuit having one or more processors and associated memory device(s) configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) may generally comprise memory element(s) including, but not limited to, computer readable medium (e.g., random access memory (RAM)), computer readable non-volatile medium (e.g., a flash memory), and/or other suitable memory elements.

Such memory device(s) may generally be configured to store suitable computer-readable instructions that, when implemented by the processor(s), configure the control circuit to perform various functions including, but not limited to, converting the signals from the sensor 106 into an audible and/or visual signal and other functions. More particularly, the instructions may configure the control circuit to perform functions such as receiving directly or indirectly signals from one or more sensors (e.g. voltage sensors, current sensors, and/or other sensors) indicative of various input conditions, and/or various other suitable computer-implemented functions, which enable the device 100 to carry out the various functions described herein. An interface can include one or more circuits, terminals, pins, contacts, conductors, or other components for sending and receiving control signals. Moreover, the control circuit may include a sensor interface (e.g., one or more analog-to-digital converters) to permit signals transmitted from any sensors within the system to be converted into signals that can be understood and processed by the processor(s).

The display 110 may provide a waveform and/or numeric value output that represents the blood velocity. The light array 112 may be a series of light emitting diodes (LEDs) that, in some embodiments, change color or, in other embodiments, are selectively illuminated to represent the blood velocity. In still other embodiments, the intensity or on/off status of the LED array may also indicate blood velocity. In yet other embodiments, haptic feedback may be used to indicate blood velocity. In addition, one or more visual, audible, tactile, or other indicators, such as LEDs, particular tones, haptic feedback, or the like, may be provided to indicate a status of the device 100. For example, a first visual indicator 114a indicates whether the device 100 is on or off. As a particular example, a green LED 114a is illuminated when the device 100 is on, and the LED 114a indicates the device 100 is off when the LED 114a is not illuminated. Further, a second visual indicator 114b indicates whether a power source 115 of the device 100, such as a battery, is sufficient to power the device 100. As a particular example, a red LED 114b is illuminated when the battery life of a battery for powering the device 100 that is disposed within the handle 102 is below a certain percentage, e.g., the LED 114b is illuminated when the battery life is 20% or less. As such, when the LED 114b is not illuminated, the second visual indicator 114b indicates to an operator that the battery life is greater than 20%, which may be sufficient to use the device 100 in a medical procedure. Other or different visual, audible, tactile, or other indicators may be used to indicate to an operator of the device 100 a status of one or more features of the device 100.

In the depicted embodiment, the handle 102 comprises one or more controls for operating the device 100. Where the device 100 provides an audible signal, the handle 102 includes one or more controls for adjusting the volume of the audible feedback source that emits the audible signal, e.g., the one or more controls are volume buttons 116 shown in FIG. 1. For example, when an operator presses a first button 116a, the volume of the audible signal delivered through the speaker 108 increases, and when the operator presses a second button 116b, the volume decreases. As further illustrated in FIG. 1, the handle 102 includes one or more controls, e.g., a power button 118, for powering the device 100 on and off. As described above, the device 100 may include an indicator for indicating whether the device 100 is on or off, and in some embodiments, rather than including a separate LED indicator or the like, the power button 118 may be illuminated when the device 100 is on, and the illumination may be extinguished when the device is off. Also, it will be appreciated that the device 100 is a fully self-contained device and, as such, is powered by a power source 115 that is disposed within the handle 102 in the exemplary embodiment of FIG. 1. That is, the handle 102 and tip 104 together form a fully self-contained unit. The power source 115 may be, e.g., one or more batteries that are single use or re-chargeable, and in embodiments in which the one or more batteries are re-chargeable, the handle 102 defines a port 120 for connecting the device 100 to a source for charging the one or more re-chargeable batteries disposed in the handle. That is, an optional charging port 120 may be provided for connecting the rechargeable power source 115 in the handle 102 to a source for re-charging the rechargeable power source 115, such as a power outlet or the like.

It will be appreciated that the device 100 may have various configurations. For instance, as illustrated in FIG. 1, the device 100 may be a single piece, i.e., the handle 102 and tip 104 may be a single integral component. In some embodiments of the single piece device 100, the device 100 may be a disposable device configured for single patient or one-time use. That is, the device 100 may be discarded after use in a single medical procedure. As such, relatively low cost materials, e.g., the material used to form the handle or housing 102, the power source, the electronics, etc., may be selected for the device 100 and/or some features of the device 100, e.g., the charging port 120, may be omitted to minimize the cost of the single-use device 100. Further, the single-use device 100 may be sterile, e.g., the device 100 may be sealed in sterile packaging that is discarded upon opening. In other embodiments, the single piece device 100 may be reusable and, more particularly, may be configured for re-sterilization after use. For example, the device 100 may be sufficiently sealed to permit the device 100 to be sterilized (e.g., by autoclaving, ethylene oxide sterilization, coating or submerging in a liquid sterilizer, etc. according to a typical sterilization protocol) after each use of the device 100. Accordingly, whether packaged in sterile packaging or configured for re-sterilization, the entire single piece device 100 may be sterile for use in an operating room (OR) or other sterile field.

Turning to FIGS. 2-4 and FIGS. 8-16, the device 100 may be a multi-piece rather than a single piece device. Referring particularly to FIGS. 2-5 and 9-13, in some embodiments, the handle 102 and tip 104 may be separate pieces rather than a single integral piece. For example, the tip 104 may be detachable from and attachable to the handle 102. As such, the tip 104 (rather than the entire device 100) may be configured for single patient or one-time use and may be discarded after use with a single patient or in a single medical procedure. Thus, as described with respect to the single piece device 100, where the tip 104 is configured for single patient or one-time use, relatively low cost materials may be used to construct the tip 104 to minimize its cost. In other embodiments, the tip 104 may be reusable and, thus, may be configured for re-sterilization (e.g., using a typical sterilization protocol as described above) after use or for non-sterile use in a clinical environment.

Figure 14:
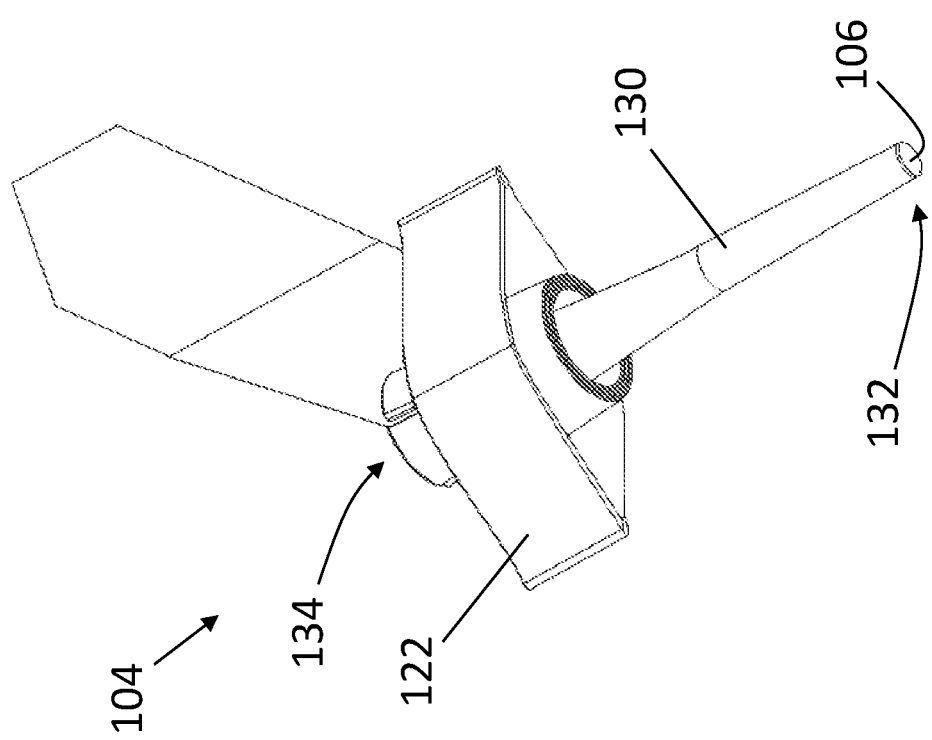
FIG. 14 provides a side, perspective view of the tip of the handheld ultrasound device of FIG. 8 having a sterile barrier, according to an exemplary embodiment of the present subject matter; the tip illustrated in FIG. 14 may be a replacement tip for the device in some exemplary embodiments of the present subject matter.
Figure 15:
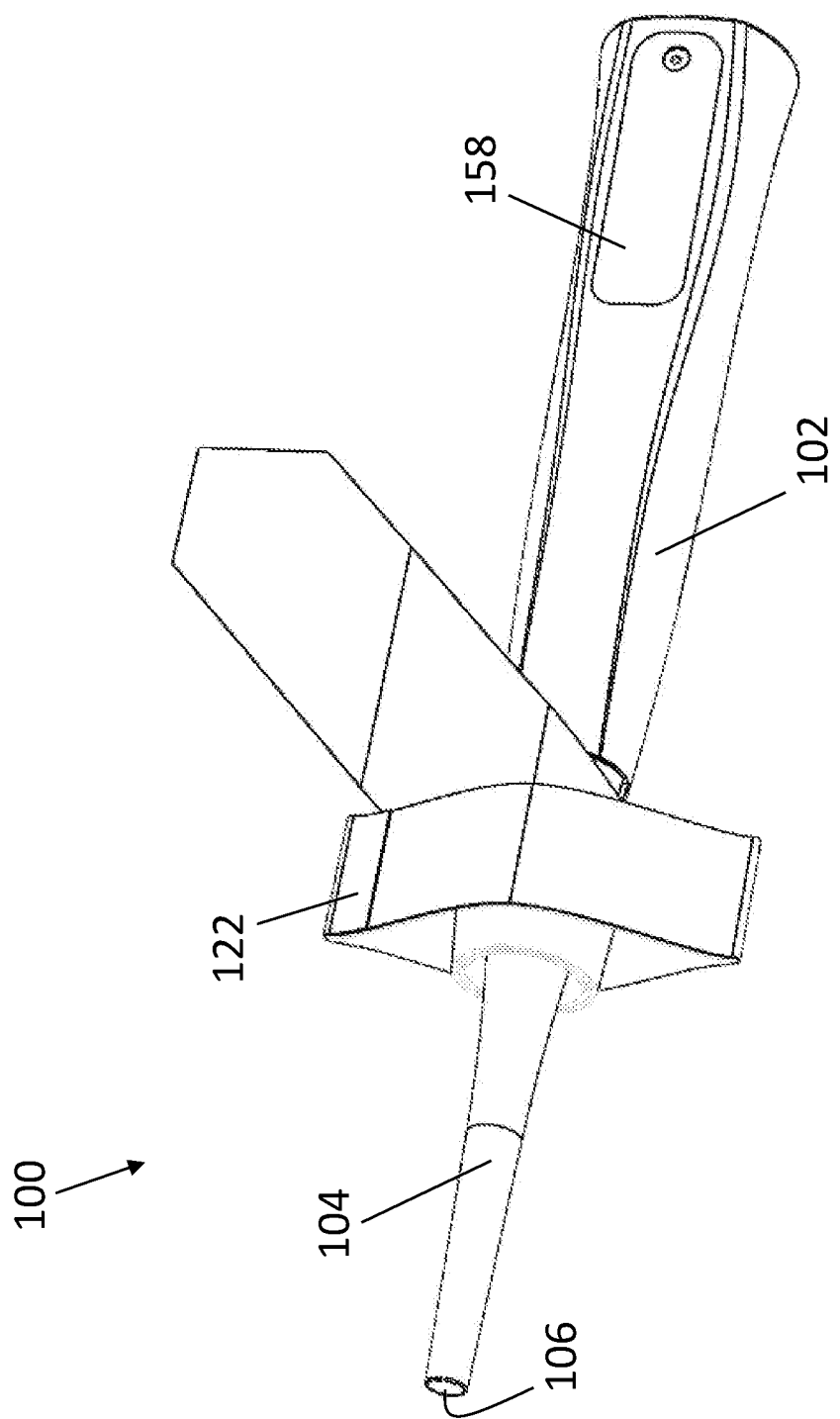
FIG. 15 provides a back, perspective view of the tip of FIG. 14 attached to the handle of FIG. 13 to form the handheld ultrasound device of FIG. 8 having the sterile barrier.
Figure 16:
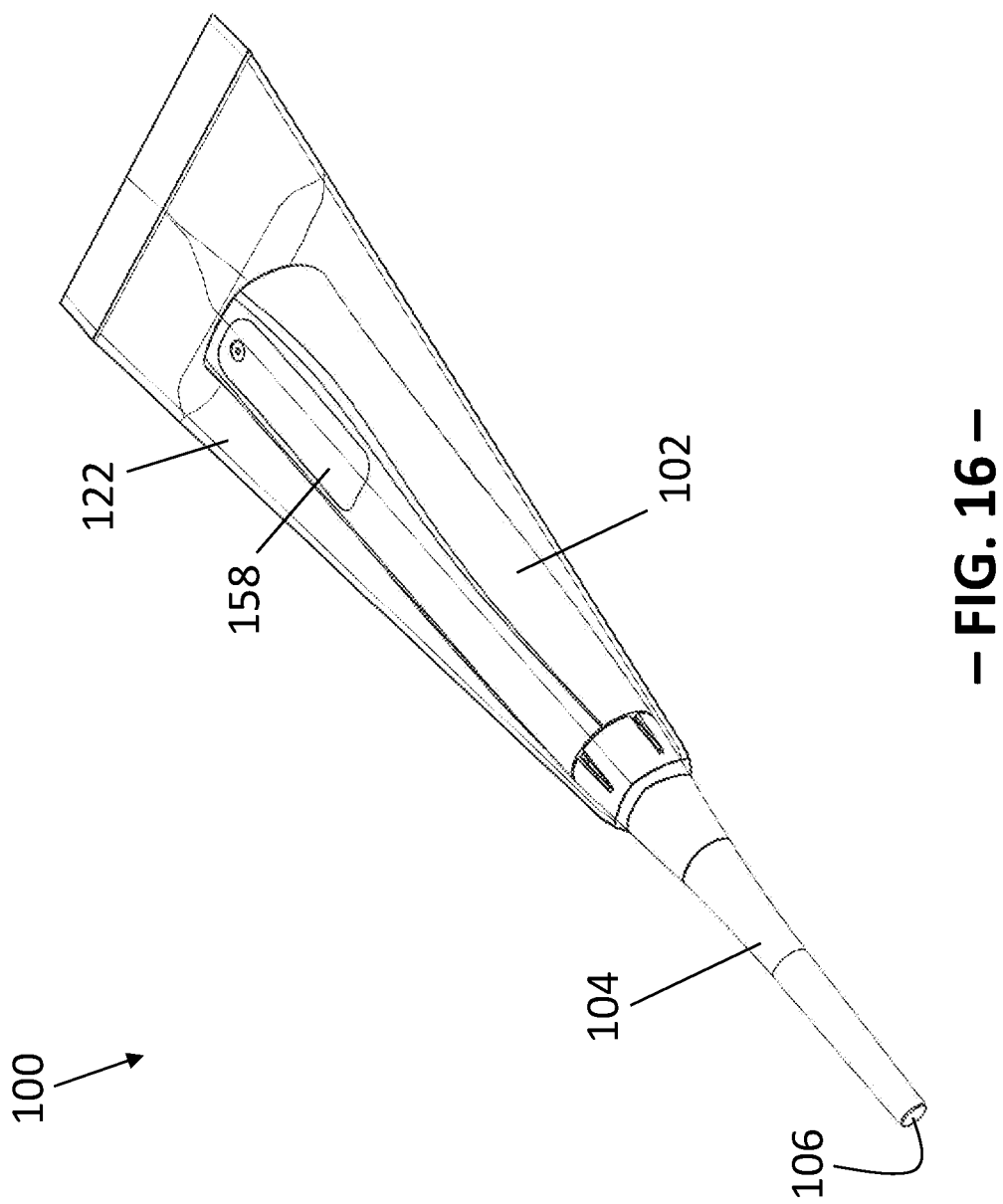
FIG. 16 provides a back, perspective view of the assembled device of FIG. 15 with the sterile barrier drawn over the handle of the device.

In either embodiment, the handle 102 may be separately sterilizable, or the device 100 may include a sterile barrier 122 that can be drawn over or around the handle 102 such that the unsterile handle 102 may be used in a sterile environment such as an OR. For example, as shown in FIGS. 2, 6, 7, and 14-16, the tip 104 includes a sterile barrier 122, which may be gathered in an accordion-type fold as illustrated in FIGS. 6 and 7 before deployment over the handle 102. As illustrated in FIGS. 14 and 15, other types of folds or gathering of the sterile barrier 122 also may be used, e.g., to keep the sterile barrier 122 with the tip 104 and/or out of the way before the tip 104 is attached to the handle 102. Further, the sterile barrier 122 may be secured to the tip 104 at different locations. In some embodiments, the sterile barrier 122 is secured to the tip 104 at or near a distal end 134 of the tip 104, as illustrated in FIGS. 2, 6, and 7. In other embodiments, such as shown in FIGS. 14-16, the sterile barrier 122 is secured to the tip 104 between a proximal end 132 and distal end 134 of the tip 104, e.g., just above or beyond the slits 164 defined in the distal end 134 of the tip 104 as depicted most clearly in FIG. 16.

To prepare the handle 102 for use in a sterile environment, the tip 104 is attached to the handle 102, and the sterile barrier 122 is in a folded position before the tip 104 is attached to the handle 102, as shown in FIGS. 6, 7, and 14. After the tip 104 is attached to the handle 102, e.g., as shown in FIG. 15, the sterile barrier 122 is deployed, e.g., by rolling the barrier 122 down over the non-sterile handle 102 and closing the barrier 122 at a distal end 124, e.g., as shown in FIGS. 2 and 16. For instance, the distal end 124 of the barrier 122 may be rolled up to close the end 124; a closure mechanism comprising male and female portions that, e.g., are pressed together to interlock the male and female portions to thereby seal the end 124; and/or a pressure sensitive adhesive, which may be protected from inadvertent or unwanted closure by a release liner, that attaches the barrier 122 to itself to thereby seal the end 124. Alternatively, the sterile barrier 122 may extend outside of the sterile field such that the distal end 124 of the barrier 122 need not be closed, i.e., the sterile barrier 122 may have a length such that its distal end 124 is outside of the sterile field and can remain open. Further, in suitable embodiments, the sterile barrier 122 may be included with the handle 102 rather than the tip 104.

As illustrated in FIGS. 2 and 16, the sterile barrier 122 may be a relatively thin transparent film that allows the controls on the handle 102, such as the volume buttons 114 and the power button 116, to be operated through the barrier 122, as well as allows the audible and/or visual signals to be communicated through the barrier 122. For instance, an audible signal emitted through the speaker 108 may be heard through the sterile barrier 122. In some embodiments, the sterile barrier 122 may be made from a thin film polymer such as urethane, polyethylene, polypropylene, or polyvinylchloride.

Referring to FIG. 3A, rather than incorporating a sterile barrier 122 as part of the device 100, in some embodiments a separate sheath 138 may be provided that fully covers the handheld device 100 to provide a sterile barrier and permit the device 100 to be used in a sterile field. Together, the handheld ultrasound device 100 and the sheath 138 form a handheld ultrasound sterile assembly 140. The sheath 138 may have a shape complementary to the shape of the device 100 and/or may be configured to conform to the shape of the device 100. For instance, as shown in FIG. 3, the sheath 138 may include a first portion 138a having a diameter $d_{sheath1}$ and length $l_{sheath1}$ complementary to the diameter $d_{shaft}$ and length $l_{shaft}$ of the tip shaft 130 of the device 100 and a second portion 138b having a width (or diameter) $w_{sheath2}$ complementary to the width $w_{handle}$ of an the handle 102 of the device 100; the second portion 138b has a length $l_{sheath2}$ that is longer than the length/handle of the handle 102 to permit sealing of the sheath 138 or to extend outside of the sterile field such that the sheath 138 does not have to be sealed. Accordingly, in the depicted embodiment, the sheath 138 has a shape complementary to the shape of the device 100 and has a relatively close fit around the device 100. However, in other embodiments, the sheath 138 may have other configurations, e.g., the sheath 138 may have substantially the same width (or diameter) $w_{sheath}$ over its entire length $l_{sheath}$ as shown in FIG. 3B. Further, like the sterile barrier 122, the sheath 138 may be formed from a relatively thin transparent film, e.g., a thin polymer film such as urethane, polyethylene, polypropylene, or polyvinylchloride.

It will be appreciated that, to prepare the device 100 for use in a sterile field (such as an OR) using the sheath 138, the tip 104 is attached to the handle 102 to assemble the device 100 and then the device 100 is inserted into the sheath 138 or the sheath 138 is drawn over the assembled device 100. Alternatively, as previously described, the device 100 may be a single piece component such that preparing the device 100 for use in a sterile field simply comprises inserting the single piece device 100 into the sheath 138 or drawing the sheath 138 over the single piece device 100. Once the device 100 is within the sheath 138, the sheath may be sealed at a distal end 139 of the sheath, similar to sealing the sterile barrier 122 at its distal end 124. Moreover, it will be understood that, because the sheath 138 is separate from the device 100, the sheath 138 may be discarded after use and the device 100 re-used in another procedure or with another patient.

As depicted in FIGS. 4 and 11-13, the handle 102 and/or the tip 104 may include a connector 126 for operatively connecting the sensor 106 and/or other electronics in or on the tip 104 to the electronics contained within the handle 102. In other embodiments, the sensor 106 may wirelessly connect to the electronics contained within the handle 102, i.e., when the tip 104 is detached from the handle 102, a wireless operative connection is established between the sensor 106 and the electronics within the handle 102 for transmitting and receiving ultrasound waves. As such, the sensor 106 can wirelessly transmit ultrasound waves, or signals derived from ultrasound waves, to a receiver 107 disposed within the handle 102. The receiver 107 may be part of a processor, controller, or other such component, which are described in greater detail herein. It will be appreciated that each of the handle 102 and tip 104 include appropriate hardware for establishing a wireless connection between the sensor 106 and the electronics. In still further embodiments, both a wireless and a hard connection between the tip 104 and the handle 102 may be used. For instance, the sensor 106 wirelessly connects to the electronics in the handle 102 while the tip 104 is used separately from the handle 102, as described herein, and the connector 126 establishes a hard connection between the tip electronics and the handle electronics when the tip 104 is attached to the handle 102. The hard connection between the tip electronics and the handle electronics can allow the sensor 106 on the tip 104 to be used with the tip 104 attached to, rather than separated from, the handle 102; can allow a power source within the tip 104, such as the power source 144 described herein, to be re-charged, e.g., when the handle 102 is connected to a power source for re-charging; and/or can allow transmission of data to and/or from the tip electronics to the handle electronics.

Further, the handle 102 and tip 104 may be configured to provide feedback that the tip 104 has been properly assembled with the handle 102. For example, the tip 104 may be coupled to the handle 102 using a friction fit, with audible feedback such as a click or snap that informs a person assembling the tip 104 with the handle 102 that the tip 104 has been properly attached to the handle 102. As illustrated in FIGS. 8-12 and 16, the tip 104 may define one or more slits 164 therein that, e.g., provide strain relief to the tip 104 as it is attached to the handle 102. As further illustrated in FIGS. 11 and 12, the tip 104 also may define a protrusion 166 that is received in a groove 168 defined in the handle 102 to help hold the tip 104 in place with respect to the handle 102. It will be appreciated that the protrusion 166 may be received in the groove 168 with an audible click or snap as described above to inform the user that the tip 104 is attached to the handle 102. In other embodiments, the tip 104 may be connected to the handle 102 via magnetic attachment. In still other embodiments, the tip 104 may be attached to the handle 102 via mechanical threads, twist lock, sliding dovetail interlock, elastomeric seal, or any number of other methods of physical attachment.

Although not illustrated in FIGS. 2-5 and 8-16, it will be appreciated that the device 100 illustrated therein may incorporate one or more features illustrated with respect to the device of FIG. 1. For example, the device 100 shown in FIGS. 2-5 and 8-16 may include a display 110, a light array 112, indicators 114a, 114b, and/or port 120. Such features may be included or defined on or by the handle 102 of FIGS. 2-5 and 8-16 in the same location or in different locations than as depicted in FIG. 1. As further depicted in FIGS. 8-17, features of the device 100, as well as the overall shape or outline of the device 100, may vary in configuration between embodiments of the device 100. For example, referring particularly to FIG. 9, the volume and power buttons 116, 118 may be round in shape rather than generally rectangular as shown in FIGS. 1-5. As another example, referring to FIG. 11, the speaker 108 may be disposed at an end surface 170 of the handle 102, rather than on a front surface 162 of the handle 102 as shown in FIGS. 1-5. Additionally, a single indicator 114 may be used to indicate a status of the device 100, although in some embodiments the single indicator 114 may be dual-colored, i.e., configured to display two different colors in a single indicator 114 location. Referring to FIG. 10, a removable cover 158 may be provided, e.g., on a back surface 160 of the handle 102 opposite the front surface 162 on which the controls 116, 118, indicator(s) 114, display 110, and/or light array 112 are disposed. The removable cover 158 can allow access to the power source 115 of the handle 102 (such as a battery or the like) and/or can allow access to one or more electronic components disposed within the handle 102, such as a printed circuit board (PCB) or the like used for electrically and/or operatively connecting the electronics within the handle 102. Further, comparing FIGS. 1, 2, 9, and 17, for example, and as described in greater detail herein, the tip 104 may have various configurations, including the shape or profile of the sensor 106, the length of the tip 104, etc. Moreover, the single piece device 100 or each of the handle 102 and tip 104 in a multi-piece device 100 may be waterproof, e.g., to be more conducive to use in a surgical setting near bodily fluids, to facilitate sterilization of the device 100 and/or its components 102, 104 for re-use following a medical procedure, etc.

Referring now to FIG. 5, in some embodiments, the tip 104 may be tethered to the handle 102 by a cable 128 such that the tip 104 may be separated or detached from the handle 102 while the device 100 is in operation and be used away from the handle 102. More specifically, some uses of the ultrasound device 100 may require the sensor 106 to be placed or positioned in a relatively narrow or tight space that will not accommodate the handle 102 or the combination of the handle 102 and tip 104. Accordingly, in embodiments of the device such as shown in FIG. 5, the tip 104 may be detached from the handle such that the sensor 106 can be used in the narrow or tight location, with the cable 128 providing operative connectivity between the sensor 106 and the electronics (e.g., the power source 115, the power switch, the processor, etc.) within the handle 102 required for the sensor 106 to be operable and to deliver the audible and/or visual signal(s) to the operator. It will be appreciated that, even with the tip 104 detached from the handle 102, the ultrasound device 100 remains a handheld device. For instance, an operator may hold the tip 104 with one hand while holding the handle 102 with the other hand. Further, the controls on either or each of the tip 104 and handle 102, such as the volume and/or power buttons 116, 118 and/or the controls 142, may be sized and/or located such that the operator can manipulate the controls while holding the handle 102 in one hand and the tip 104 in the other hand.

As further illustrated in FIG. 5, the tip 104 may be sized and dimensioned for use in such narrow or tight locations. More particularly, the illustrated tip 104 has an elongated narrow shaft 130, and the sensor 106 is positioned on a proximal end 132 of the tip 104, at one end of the shaft 130. In an exemplary embodiment, the shaft 130 may be about four to about five centimeters (about 4-5 cm) in length with a diameter of about one centimeter (about 1 cm) or less. Further, a distal end 134 of the tip 104 may define a cavity 136 in which the cable 128 may be contained or stored when the tip 104 is attached to the handle 102.

Regardless of whether the device 100 is a single piece or multi-piece device, the tip 104 may have a different configuration, including a different shape and/or size, for use in different medical procedures. As one example, the tip 104 for use in a gastrointestinal procedure may have a different stiffness, shape, and/or size than the tip 104 for use in a cardiology procedure. As such, for embodiments in which the device 100 is a single piece, different devices 100 may be provided for different procedures, with the devices for the different procedures differing at least as to the configuration of their tips 104. For embodiments in which the device 100 utilizes tips 104 that are formed separately from the handle 102 and are attachable to the handle 102, one tip 104 may be attached to the handle 102 for one procedure, and a different tip 104 may be attached to the handle 102 for a different procedure. That is, the same handle 102 may be used for different procedures, with a tip 104 specific to the respective procedure attached to the handle 102. Further, the tip 104 may have different configurations for use in different portions of a single procedure; e.g., a first tip 104 may be used in a first area of a patient's body while a second tip 104 may be used in a second area of the patient's body.

As examples of aspects of the tip 104 that may vary between embodiments, in some embodiments, the tip 104 may be flexible, semi-flexible, rigid, or semi-rigid. In other embodiments, the tip 104 may incorporate a curvature, bend, or angle along its length, e.g., as illustrated in FIG. 1 where the tip 104 is curved near the sensor 106, and in exemplary embodiments, the radius of curvature is at most 90° (i.e., less than or equal to 90°). For instance, the tip 104 may be configured for use in procedures in which the velocity of blood is measured in blood vessels behind the heart (as with respect to the direction from which the heart is approached with the device 100), and the tip 104 includes a curve, bend, or angle sufficient to allow the sensor 106 to be positioned behind the heart, i.e., the tip 104 is angled, bent, or curved to allow access to the blood vessels by the sensor 106. In yet other embodiments, the tip 104 may be permanently deformable, e.g., an operator may bend the tip 104 and the tip 104 remains in the bent configuration, or temporarily deformable, e.g., an operator may bend the tip 104 and the tip 104 remains in the bent configuration for a period of time before returning to a default configuration, such that the operator can customize the shape of the tip 104. For example, the tip shaft 130 may be formed from a material that permits deformation of the shaft 130 to a desired shape and retention of the desired shape. Of course, it will be appreciated that the tips 104 may incorporate other differences as well, e.g., a diameter of the shaft 130 and/or a length of the shaft 130 may vary between tips 104.

As described herein, the handheld ultrasound device 100 may be a multi-piece device comprising a handle 102 and a separate tip 104, such that the tip 104 may be a replaceable component of the device 100 and provided separately from the device 100 as shown in FIG. 6. As an example, the tip 104 may be configured for single use, and a new sterile tip 104 may be attached to the handle 102 for each use of the device 100, with each tip 104 being discarded after use. However, in other embodiments, the replaceable tip 104 may be configured for multiple uses and have features allowing the tip 104 to be sterilized after use. As previously described, whether configured for single patient use, one-time use, or to be re-sterilized, at least some embodiments of the replaceable tips 104 may incorporate a sterile barrier 122, which may be deployed over or around the handle 102 to allow a non-sterile handle 102 to be used in a sterile environment such as an OR. Additionally, each replaceable tip 104 includes at least one sensor 106 and features for operatively coupling the at least one sensor 106 to the controls housed in the handle 102, e.g., via a connector 126. In some embodiments, the replaceable tip 104 has a shaft 130, which separates the at least one sensor 106 from the handle 102, i.e., the at least one sensor 106 is disposed on a proximal end 132 of the shaft 130 and the opposite distal end 134 of the shaft 130 is configured for attaching the tip 104 to the handle 102. In other embodiments, the tip 104 may be configured for operative coupling or tethering to the handle 102, e.g., wirelessly or via a cable 128, such that the at least one sensor 106 may be operated away from the handle 102. A cable 128 may be provided with the replaceable tip 104, such that a new cable 128 is provided with each tip 104, or the handle 102 may comprise the cable 128, such that the cable 128 need not be replaced each time the tip 104 is replaced. In either embodiment, a distal end 134 of a shaft 130 of the tip 104 may define a cavity 136 for housing the cable 128 when the tip 104 is attached to the handle 102.

Moreover, as shown in FIG. 7, the tip 104 may include one or more controls 142 for operating or controlling the device 100 when the tip 104 is operated away from the handle 102. For example, the tip 104 may include a power source 144, such as one or more batteries, and the one or more controls 142 includes a control 142a for activating or deactivating the power source. Where the power source 144 is a rechargeable battery or the like, the tip 104 also may include a port 146 for connecting the rechargeable power source 144 to a charging source; i.e., an optional charging port 146 may be provided for connecting the rechargeable power source 144 in the tip 104 to a charging source such as a power outlet. As another example, the one or more controls 142 located on the tip 104 may include controls for adjusting or controlling feedback from the sensor 106, e.g., volume buttons 142b, 142c for adjusting the volume of an audible feedback source such as the speaker 108. In appropriate embodiments, the tip 104 also may incorporate one or more sources of feedback, e.g., the tip 104 may include an LED light array similar to the light array 112 shown in FIG. 1 for providing visual feedback of the ultrasound waves received by the sensor 106. It will be appreciated that the power source, controls 142, and/or feedback sources of the tip 104 may be in addition to or as an alternative to the power source, controls 116, 118, etc., and feedback sources of the handle 102.

Further, two or more different configurations of replaceable tips 104 may be provided such that one configuration of tip 104 may be used for one procedure and a different configuration of tip 104 used for a different procedure. Thus, the device 100 may be configured for use in different procedures by merely attaching or operatively coupling a different tip 104 to the handle 102. That is, different tips 104 may be attached to the handle 102, e.g., at a connector 126 or using a cable 128, or may be operatively connected to the handle 102 through a wireless connection.

Additionally, although described primarily with respect to FIGS. 6 and 7, it will be appreciated that replaceable tips 104 for the device 100 may have any appropriate configuration. For example, the tips 104, which may be available for purchase separately from the device 100 and/or handle 102, can have any of the tip configurations illustrated and described herein, as well as any other configurations within the scope of the present subject matter. As a particular example, the tip 104 illustrated in FIGS. 8-12 may be provided as a separate component, the tip 104 illustrated in FIG. 17 may be provided as a separate component, and/or the tip 104 illustrated in FIGS. 14-16, having a sterile barrier 122, may be provided as a separate component. Therefore, tips 104 having any number or variety of configurations may be produced and procured separately from the device 100 and/or handle 102.

Referring to FIG. 8, in some embodiments, the handheld ultrasound device 100 may be received in a docking station 148, e.g., to re-charge a power source 115, 144 within the handle 102 or tip 104, to transfer data or other information from the device 100 to a processing device such as a computer or the like, etc. For instance, rather than including charging ports 120 and/or 146, the device 100 may include one or more openings 150 (FIG. 11) for receipt of one or more prongs (not shown) of the docking station 148, through which an electrical connection is established to re-charge the one or more power sources within the device 100. The docking station 148 includes one or more features for supporting the device 100. For example, the docking station 148 defines a depression 152 in which the device 100 is received, and the docking station 148 includes a support segment 154 that contacts at least a portion of the device 100, e.g., to keep the device 100 in an upright position and/or to maintain the charging prong(s) of the docking station 148 within the opening(s) 150 of the device 100. Further, the docking station 148 also may include one or more features for indicating the status of the device 100 to a user of the device 100. In the depicted embodiment, the docking station 148 includes an indicator 156, which may be an LED light or the like for indicating to the user whether the device 100 is charging. Other indicators 156 may be provided, e.g., to indicate to the user whether the device 100 is transferring data to a separate device or any other state or status of the device 100.

Accordingly, as described herein, the handheld ultrasound device 100 is a fully self-contained Doppler ultrasound device. That is, the device 100 incorporates all features needed to transmit and receive ultrasound waves, as well as convert such waves into one or more signals that may be understood by an operator of the device 100 to indicate an assessed value, e.g., the strength and/or pattern of blood flow through a blood vessel. Thus, the handheld device 100 described herein may be operated entirely in a sterile field, e.g., by a doctor or clinician in a clinical setting or a surgeon in a surgical setting, which can eliminate a cord between a sensor tip in the sterile field or environment and a receiver outside the sterile field (which could be a trip hazard in a surgical setting), as well as eliminate a second operator to manage a portion of the device's operation (e.g., outside the sterile field). Moreover, the various embodiments of the device 100 illustrated and described herein have a stylus-like form factor, which reduces the overall footprint of the device. The reduced footprint and self-contained nature of the device 100 make handheld Doppler ultrasound more conducive to clinical and surgical use. In addition, the reduced size of the device 100 allows the device 100 to be protected by a sterile barrier 122 as described herein, or may reduce the cost of forming the device 100 (or its components, such as tip 104) as a single patient or one-time use sterile device.

Further, the device 100 may be a single piece device configured for single patient use, one-time use, or for multiple uses. For example, the single piece device 100 may be a sterile device (e.g., may be provided in sterile packaging) that is disposed of after a single use or that is configured for re-sterilization after each use. In other embodiments, the device 100 may be a multi-piece device that comprises a handle 102 and a separate tip 104; the tip 104 includes at least one sensor 106 for transmitting and receiving ultrasound waves. As such, the tip 104 may be a replaceable component, which allows (1) a new sterile tip 104 to be used for each procedure while the handle 102 may be re-used for multiple procedures or (2) a different configuration of tip 104 to be used for different procedures while the same handle 102 is used for the different procedures. In such embodiments, the tip 104 may incorporate a sterile barrier 122 such that the handle 102 need not be a sterile component of the device 100; rather, the sterile barrier 122 ensures the sterility of the handle 102 such that the device 100, including a sterile tip 104 and a handle 102 enclosed within a sterile barrier 122, may be used in a sterile environment such as an OR. Other advantages of the subject matter described herein also may be realized by those of ordinary skill in the art.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A handheld ultrasound device, comprising:
   a handle;
   a tip comprising a sensor for transmitting and receiving ultrasound waves, the tip having a distal end and a proximal end, the sensor positioned at the proximal end;
   a sterile barrier secured to an outer surface of the tip between the proximal end and the distal end, the sterile barrier extending distally from the tip to enclose the handle; and
   a receiver disposed within the handle, the receiver configured to receive ultrasound waves from the sensor,
   wherein the tip having the sensor is separable from the handle, and
   wherein the handle and tip are a fully self-contained unit configured to provide feedback of a patient's blood velocity to a user without connecting to another device.

2. The handheld ultrasound device of claim 1, wherein the tip is operatively coupled to the handle via a connector.

3. The handheld ultrasound device of claim 1, wherein the tip is operatively coupled to the handle via a wireless connection.

4. The handheld ultrasound device of claim 3, wherein the sensor wirelessly transmits the ultrasound waves to the receiver disposed within the handle.

5. The handheld ultrasound device of claim 1, wherein the tip is tethered to the handle via a cable for operation when separated from the handle.

6. The handheld ultrasound device of claim 5, wherein the distal end of the tip removably couples the tip to the handle, and wherein the distal end of the tip defines a cavity for storing the cable when the tip is attached to the handle.

7. The handheld ultrasound device of claim 1, wherein the tip is sterile.

8. The handheld ultrasound device of claim 1, wherein the tip having the sensor is replaceable.

9. The handheld ultrasound device of claim 1, wherein the tip having the sensor is sterile and is configured for re-sterilization after use.

10. The handheld ultrasound device of claim 1, wherein the tip having the sensor is sterile and is configured for one-time use.

11. The handheld ultrasound device of claim 1, wherein the handle includes a speaker, and wherein the speaker is configured to provide audible feedback corresponding to the patient's blood velocity.

12. The handheld ultrasound device of claim 1, wherein the handle includes a display, and wherein the display is configured to provide visual feedback corresponding to the patient's blood velocity.

13. The handheld ultrasound device of claim 1, wherein the handle includes a light array, and wherein the light array is configured to provide visual feedback corresponding to the patient's blood velocity.

14. A handheld ultrasound device, comprising:
    a handle;
    a tip comprising a sensor for transmitting and receiving ultrasound waves, the tip having a distal end and a proximal end, the sensor positioned at the proximal end; and
    a sterile barrier secured to an outer surface of the tip between the proximal end and the distal end, the sterile barrier extending distally from the tip to enclose the handle.

15. The handheld ultrasound device of claim 14, wherein the tip includes a shaft, and wherein the shaft defines the proximal end such that the sensor is positioned on a proximal end of the tip at the proximal end of the shaft.

16. A handheld ultrasound device, comprising:
    a handle including a receiver and a feedback device for providing feedback corresponding to a patient's blood velocity to a user;
    a tip removably coupled to the handle, the tip comprising a sensor for transmitting and receiving ultrasound waves, the tip having a distal end and a proximal end, the sensor positioned at the proximal end; and
    a sterile barrier secured to the tip between the proximal end and the distal end, the sterile barrier extending distally from the tip to enclose the handle,
    wherein the proximal end of the tip is not enclosed within the sterile barrier, and
    wherein the tip having the sensor is disposable.

17. The handheld ultrasound device of claim 16, wherein the handle includes one of a protrusion or a groove at a proximal end of the handle and the tip includes the other of the protrusion or the groove at the distal end of the tip, the groove configured to receive the protrusion to secure the tip to the handle.

18. The handheld ultrasound device of claim 16, wherein the receiver is configured to receive ultrasound waves from the sensor and the feedback device is operably connected to the receiver.

* * * * *